United States Patent [19]

Tykwinski

[11] 4,141,375
[45] Feb. 27, 1979

[54] KNEE CRUTCH-CANE

[76] Inventor: Leonard M. Tykwinski, 910 First Ave., Cadillac, Mich. 49601

[21] Appl. No.: 875,113

[22] Filed: Feb. 3, 1978

[51] Int. Cl.² .......................... A61H 3/02; A45B 9/02
[52] U.S. Cl. ...................................... 135/66; 135/68; 135/76; 135/78; 135/84
[58] Field of Search ...................... 135/66, 68, 77, 84, 135/76, 78

[56] References Cited

U.S. PATENT DOCUMENTS

| 875,482 | 12/1907 | Wyatt | 135/68 X |
|---|---|---|---|
| 994,194 | 6/1911 | Pratt | 135/84 X |
| 1,120,305 | 12/1914 | Graves | 135/68 |
| 1,183,726 | 5/1916 | Gregson | 135/68 |
| 2,378,486 | 6/1945 | Jones | 135/68 |
| 2,453,742 | 11/1948 | Bowen et al. | 135/77 |
| 2,568,654 | 9/1951 | Neptune | 135/68 X |
| 2,678,054 | 5/1954 | Bostelman | 135/68 |
| 2,778,370 | 1/1957 | Chamblee | 135/68 |
| 3,199,886 | 8/1965 | Dover | 135/84 X |
| 3,949,773 | 4/1976 | Marescalco | 135/78 |

*Primary Examiner*—Price C. Faw, Jr.
*Assistant Examiner*—Conrad L. Berman
*Attorney, Agent, or Firm*—Clarence A. O'Brien; Harvey B. Jacobson

[57] ABSTRACT

An upright is provided including upper and lower ends and the lower end of the upright includes a foot for frictionally gripping an upwardly facing support surface. The upper end of the upright defines a pair of horizontally spaced apart opposite side portions between which a horizontal upwardly opening cradle is supported for angular adjustment about an axis extending transversely of the cradle and between the opposite side portions. One of the opposite side portions includes a cane handle supported therefrom for angular displacement about its longitudinal axis and projecting above the cradle and one end of the cradle includes an outwardly convex end wall while the other end of the cradle is open and includes an endwise outwardly projecting support arm from whose outer end a second upwardly opening cradle is supported.

29 Claims, 14 Drawing Figures

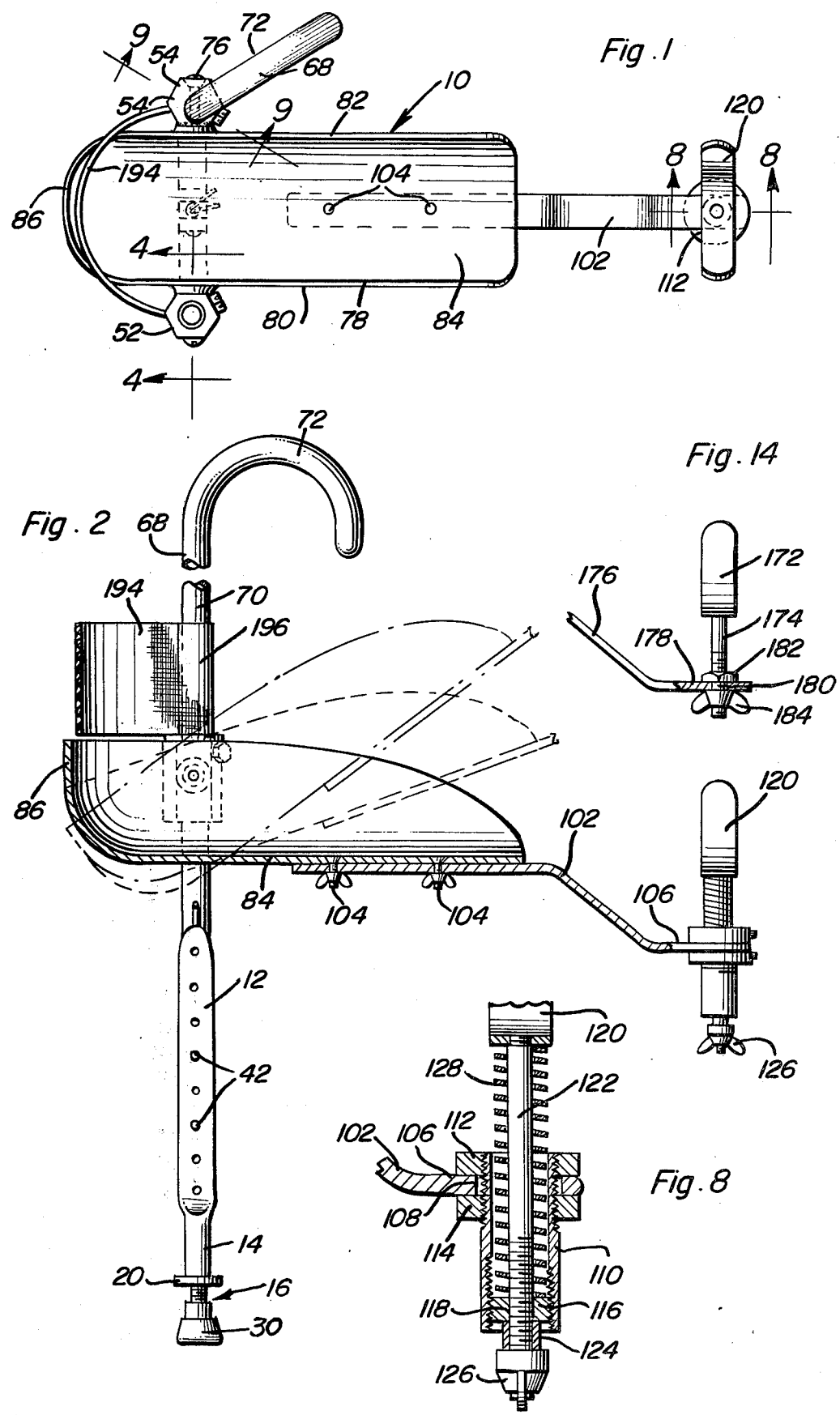

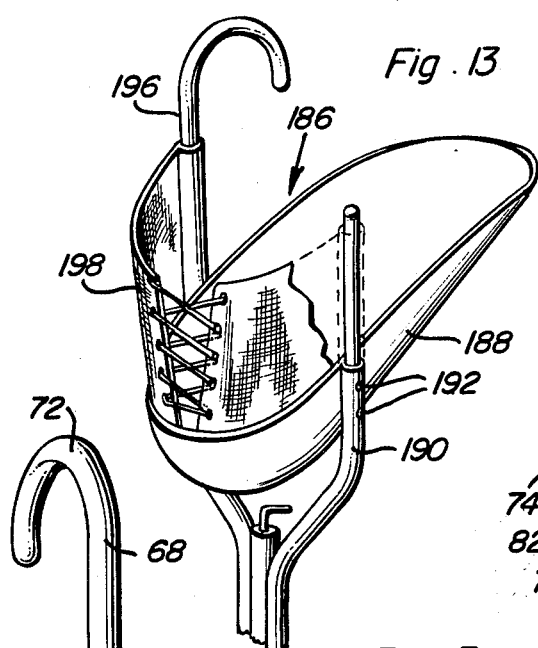
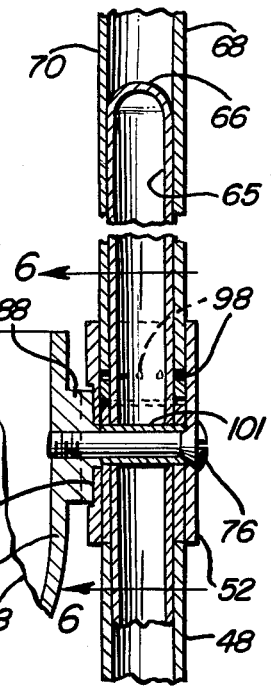
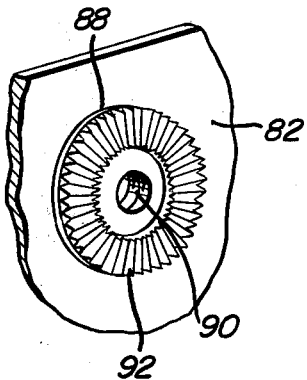
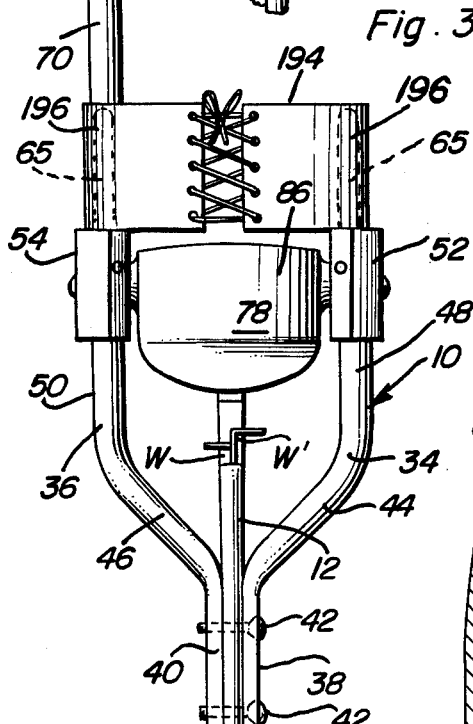
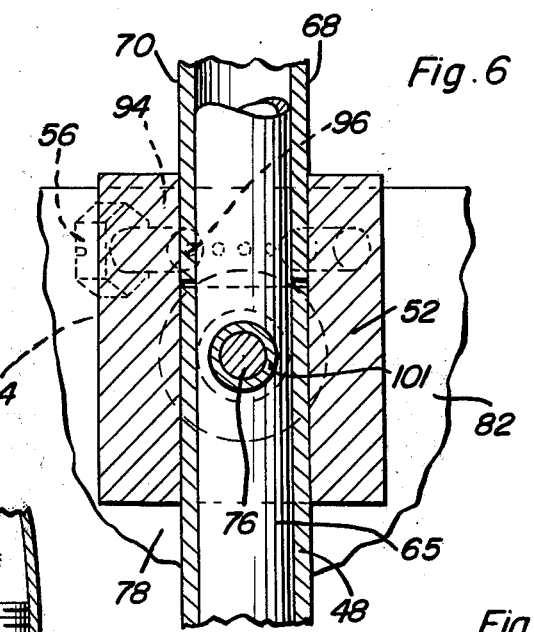
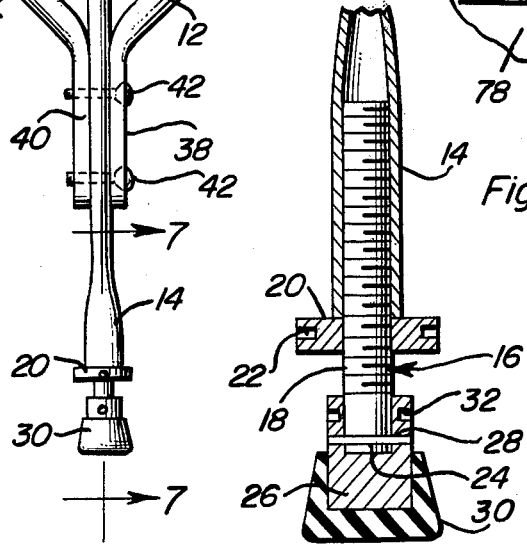
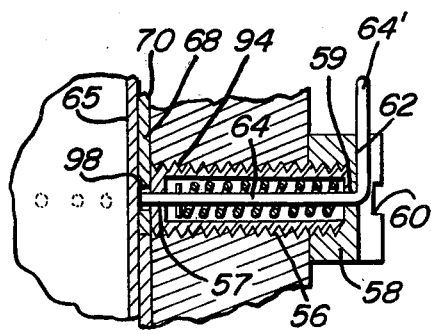

KNEE CRUTCH-CANE

BACKGROUND OF THE INVENTION

There are many instances in which persons having injured legs are required to walk with the lower leg portion of the injured leg maintained in a substantially horizontal position. Although such persons may use a strap to maintain that lower leg portion in a substantially horizontal position and may use crutches to enable them to be ambulatory or such persons may use a single crutch provided with a horizontal cradle for support of the lower leg portion of their injured leg, walking with crutches or a single crutch is very difficult and tiring. Accordingly, a need exists for a cane-type structure which may be used to support the weight of one leg with the lower leg portion thereof in a horizontal position, walking through the utilization of a cane being more comfortably accomplished with less tiring effect upon the user of such an apparatus.

Examples of various forms of crutches and other related structures including some of the general structural and operational features of the instant invention are disclosed in U.S. Pat. Nos. 108,303, 875,482, 994,194, 2,678,054, 2,,778,370 and 3,199,886.

BRIEF DESCRIPTION OF THE INVENTION

The crutch-cane of the instant invention has been specifically designed for use by persons who must maintain the lower leg portion of one leg horizontal. The crutch-cane enables such periods to be ambulatory with relative ease and comfort.

The main object of this invention is to provide a crutch-cane construction for use by persons who must maintain one lower leg portion in a generally horizontal position during walking movements.

Another object of this invention is to provide an apparatus in accordance with the preceding object and which may be readily adjusted for persons of different sizes.

Still another object of this invention is to provide a crutch-cane including a rotatably supported upper cane handle.

A further object of this invention is to provide a crutch-cane in accordance with the preceding objects and including a horizontal upwardly opening cradle in which to cradle the corresponding lower leg portion.

Still another object of this invention is to provide a structure in accordance with the immediately preceding object and enabling the cradle to be angularly adjusted about a horizontal transverse axis.

A further object of this invention is to provide a crutch-cane including a universally supported lower horizontally enlarged foot.

Still another object of this invention is to provide a crutch-cane in accordance with the preceding objects and including a cane handle vertically shiftable relative to the remainder of the crutch-cane and including structure whereby the cane handle increasingly yieldingly resists both up and down movement relative to the remainder of the crutch-cane.

Another very important object of this invention is to provide a crutch-cane which may be readily folded into a compact state.

A final object of this invention to be specifically enumerated herein is to provide a crutch-cane in accordance with the preceding objects and which will conform to conventional forms of manufacture, be of simple construction and easy to use so as to provide a device that will be economically feasible, long lasting and relatively trouble-free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a top plan view of a first form of crutch-cane constructed in accordance with the present invention;

FIG. 2 is a fragmentary, enlarged, longitudinal, vertical, sectional view of the crutch-cane illustrated in FIG. 1;

FIG. 3 is a front elevational view of the crutch-cane illustrated in FIGS. 1 and 2;

FIG. 4 is an enlarged, fragmentary, transverse, vertical, sectional view taken substantially upon the plane indicated by the section line 4—4 of FIG. 1;

FIG. 5 is a fragmentary, perspective view of one side portion of the cradle portion of the crutch-cane illustrating the circular arranged serrations thereon by which the cradle may be releasably locked in angularly adjusted positions about a horizontal transverse axis;

FIG. 6 is an enlarged, fragmentary, vertical, sectional view taken substantially upon the plane indicated by the section lines 6—6 of FIG. 4;

FIG. 7 is a fragmentary, enlarged, vertical, sectional view taken substantially upon the plane indicated by the section line 7—7 of FIG. 3;

FIG. 8 is an enlarged, fragmentary, vertical, sectional view taken substantially upon the plane indicated by the section line 8—8 of FIG. 1;

FIG. 9 is an enlarged vertical sectional view taken substantially upon the plane indicated by the section line 9—9 of FIG. 1;

FIG. 13 is a fragmentary, perspective view of a second modified form of crutch-cane; and FIG. 14 is a fragmentary, side elevational view illustrating a modified form of rear cradle for use with the crutch-cane illustrated in FIGS. 1 through 8.

DETAILED DESCRIPTION OF THE INVENTION

Figure 10:
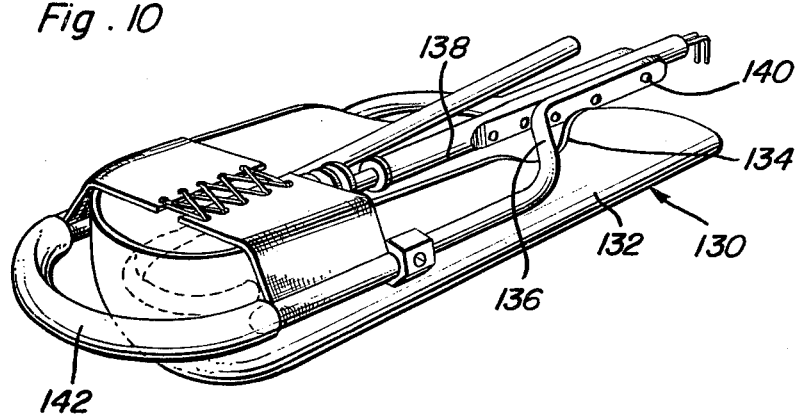
FIG. 10 is a perspective view of a modified form of crutch-cane adapted for compact folding and with the modified crutch-cane in a folded condition.
Figure 11:
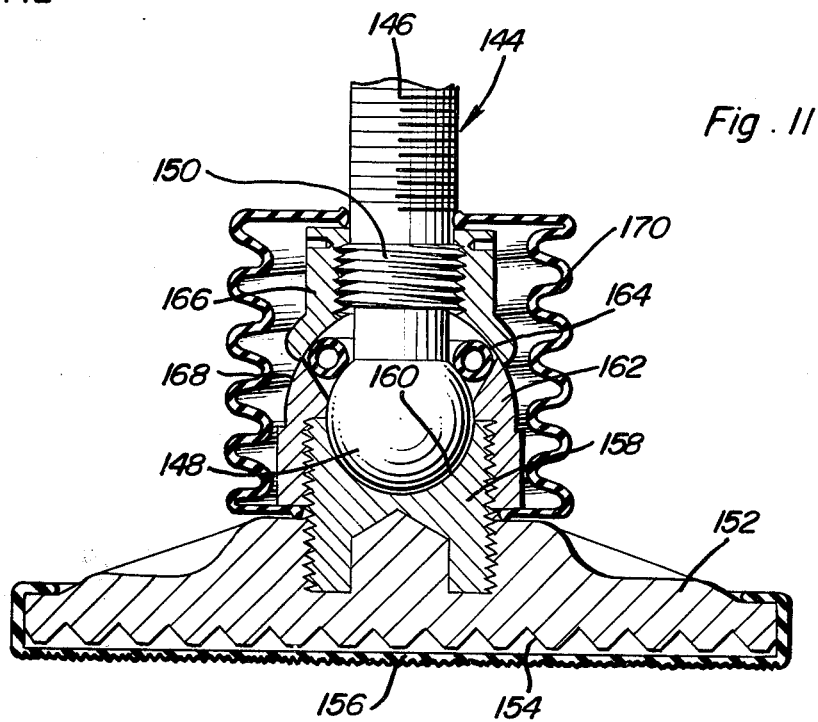
FIG. 11 is an enlarged, fragmentary, vertical, sectional view illustrating a modified form of universally supported lower foot for use with either crutch-cane illustrated in FIGS. 2 and 10.
Figure 12:
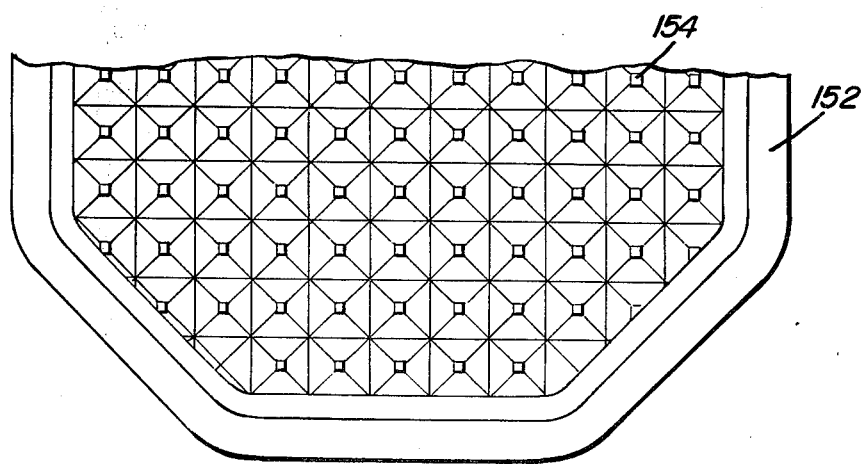
FIG. 12 is a fragmentary, bottom, plane view of the foot illustrated in FIG. 11, but with the cover therefor removed.

Referring now more specifically to the drawings, the numeral 10 generally designates a first form of crutch-cane assembly constructed in accordance with the present invention. The assembly 10 is disposed upright and includes a lower central upstanding member 12 which is diametrically enlarged at its lower end as at 14 and internally threaded. A foot assembly generally referred to by the reference numeral 16 is provided and includes an upstanding shank portion 18 which is threaded and threadedly engaged in the lower end portion 14. A jamb nut 20 provided with circumferentially spaced radial blind bores 22 is threaded on the shank portion 18 below the end portion 14 and is engageable with the latter. The lower end of the shank portion 18 includes a diametric bore 24 formed therethrough and an end cap 26 is telescoped upwardly over the lower end of the shank portion 18 and removably secured thereon against rotation relative thereto by means of a diametric pin 28 removably secured through the end cap 26 and the diametric bore 24, the end cap 26 having a crutch tip 30 removably telescoped over the lower end thereof and being provided with circumferentially spaced radial blind bores 32 above the tip 30 for a purpose to be hereinafter more fully set forth.

The assembly 10 further includes a pair of opposite side upright members 34 and 36 including lower end portions 38 and 40 between which the upper portion of the member 12 is clampingly secured by means of fasteners 42. The members 34 and 36 include upwardly and outwardly oppositely inclined midportions 44 and 46 which terminate upwardly in horizontally spaced apart upper end portions 48 and 50. The portions 48 and 50 have sleeve blocks 52 and 54 mounted thereon and each sleeve block 52 and 54 includes a set screw 56 having a counterbore equipped central bore 57 formed therethrough and provided with a head 58 on its outer end including a central bore 59. The heads 58 include circumferentially spaced shallow and deep radial grooves 60 and 62 in the end faces thereof opening into the bore 59 and L-shaped spring biased latch pins 64 are slidable through and rotatable in the bores 57 and 59 and include lateral short legs 64' which may be alternately seated in the grooves 62 and 60 to extend and retract, respectively, the ends of the pins 64 relative to the ends of the bores 57 remote from the heads 58.

The upper ends of the upper end portions 48 and 50 have pipe sections 65 telescoped therein and the exterior surfaces of the sections 65 are smooth and the sections 65 include rounded closed upper end walls 66. A short tubular cane 68 is provided including a hollow cylinder shank 70 and a reversely bent upper end hand grip 72. The shank 70 may be removably downwardly telescoped over the upper end of either section 65 and it will be noted that the opposing surfaces of the shank and sections 65 are smooth and close fitting whereby downward telescoping movement of the shank on the associated section 65 will cause the air trapped within the cane 68 to be compressed. Accordingly, downward movement of the cane 68 toward the upper end of the corresponding upper end portion 48 or 50 will be progressively yieldingly resisted. Further, forceful downward seating of the cane 68 to its lowermost position with the lower end of the shank abutted against the corresponding upper end portion 48 or 50 will cause some of the compressed air within the cane 68 to be expelled therefrom between the opposing surfaces of the interior of the shank 70 and the associated section 65. After a portion of the air trapped within the cane 68 has been expelied therefrom, upward movement of the cane 68 toward a position completely disengaged with the corresponding section 65 will be progressively yielding resisted and the cane 68 will assume a midposition on the corresponding section 65 between the lower limit position of movement thereon and an upper position in which the cane 68 will become disengaged from the corresponding upper end portion 48 or 50.

The opposing sides of the sleeve blocks 52 include circularly arranged serrated surfaces 74, see FIG. 4, and a through bolt 76 is passed through each sleeve block 52 and 54 and the corresponding upper end portions 48 and 50. An elongated generally horizontal and upwardly opening cradle 78 is provided and is received between the upper end portions 48 and 50. The cradle 78 includes opposite side longitudinal walls 80 and 82 interconnected by means of an upwardly opening semi-circular bottom wall 84 extending therebetween and one end of the cradle 78 is closed by means of a quarter spherical end wall 86. The outer surfaces of the opposite side longitudinal walls 80 and 82 include mounting bosses 88, see FIGS. 4 and 5, and threaded bores 90 formed therethrough. In addition, the walls 80 and 82 include circularly arranged serrations 92 which mate with the corresponding serrations 74 and the through bolts 76 are threadedly engaged in the bores 90 whereby the cradle 78 is supported between the support blocks 52 and 54 for angular adjustment about a horizontal transverse axis defined by the through bolts. Of course, the through bolts 76 may be loosened and the cradle 78 may be angularly adjusted as desired after which the through bolts may again be tightened in order to lock the cradle 78 in adjusted angularly displaced position.

Further, a plurality of radial bores 98 are formed in and about the lower end of the shank 70 of the cane 68 and the extendible end of the corresponding pin 64 is receivable in selected radial bore 98 to releasably retain the cane in adjusted rotated position relative to the corresponding sleeve block. Of course, when the short leg 64' is seated in one of the shallow grooves 60, the pin 64 is retracted from the opening 98 and the cane 68 is free to be rotated and shifted slightly upwardly relative to the corresponding section 65.

It may be seen from FIGS. 4 and 6 of the drawings that the sections 65 are telescoped downwardly therein and that the closed upper end walls 66 comprise the closed upper ends of the sections 65. Further, the sections 65 extend downwardly through the vertical extent of the upper end portions 48 and 50 and the through bolts 76 are received through sleeves 101 secured through the upper end portions 48 and 50 and the sections 65.

The assembly 10 further includes a rearwardly projecting support arm 102 supported from the rear portion of the bottom wall 84 by means of fasteners 104 and the rear end 106 of the support arm 102 is downwardly offset and has a vertical bore 108 formed therethrough. A support sleeve 110 has its upper end secured through the bore 108 by means of jamb nuts 112 and 114 threadedly engage with the sleeve 110 above and below the rear end portion 106 and the lower end of the sleeve 110 is internally threaded and has an abutment 116 threadedly engaged therein having an upstanding central bore 118 formed therethrough. A rear cradle 120 is supported from the upper end of a shank 122 vertically slidable through the sleeve 110 and the lower end of the shank 122 is externally threaded and has a jamb nut 124 threadedly engaged thereon abuttingly engageable with the abutment 116, the lower end of the shank 122 including a thumb nut 126 below the jamb nut 124. Further, a compression spring 128 is disposed about the shank 122 between the cradle 120 and the abutment 116 with the lower end of the spring 128 telescopingly received within the sleeve 110. Accordingly, the cradle 120 is supported for vertical shifting relative to the rear end portion 106 and is yieldingly biased toward an upper limit position.

Referring now more specifically to FIG. 10 of the drawings, the numeral 130 generally designates a modified form of assembly similar to the assembly 10 but whose cradle 132 has its opposite side walls notched as at 134 to receive the angulated portions 136 corresponding to the portions 44 and 46. In addition, from FIG. 10 of the drawings it may be seen that the member 138 corresponding to the member 12 may be reversed in position by removal of one of the fasteners 140 corresponding to the fasteners 42. Further, the assembly 130 is provided with a U-shaped tubular member 142 removably telescoped over those components of the assembly 130 corresponding to the sections 100 in order to protect those corresponding portions while the assembly 130 is in a folded compact state. Still further, the member 138 corresponding to the member 12 includes a foot assembly referred to in general by reference numeral 144 which is considerably different from the foot assembly 16 provided on the assembly 10. The foot assembly 144 includes a shank portion 146 corresponding to the shank portion 18 but which includes a ball member 148 on its lower terminal end and a diametrically enlarged threaded portion 150 spaced above the ball 148. A diametrically enlarged foot 152 is provided and includes a diamond pattern embossed undersurface 154 as well as a removable non-slip panel 156 disposed beneath the undersurface 154. The foot 152 includes a threaded supported and upwardly projecting fitting 158 defining and upwardly opening hemispherical socket 160 and a threaded universal union member 162 is threadedly engaged over the exterior of the fitting 158 and captively retains the ball member 148 in the socket 160. The opposing surfaces of the ball member 148 and the socket 160 are to be lubricated and an O-ring 164 which also serves as a cushion member is disposed about the upper portion of the ball member 148 and a downwardly opening generally hemispherical socket defining fitting 166 is threadedly supported from the threaded portion 150 of the shank 146 and is slidable, in a universal fashion, over the partial spherical outer surfaces 168 of the other portion of the fitting 162. Further, a flexible corrugated boot 170 is disposed about the fittings 162 and 166 and thereby protects the relatively movable and opposing surfaces of the fittings 162 and 166 and the fitting 158 and the ball 148 from the elements, the upper end of the boot 170 fitting tightly about the lower end of the shank 146 and the lower end of the boot 170 fitting tightly about the fitting 158 below the fitting 162.

With attention now invited more specifically to FIG. 14 of the drawings, there will be seen a modified form of rear cradle referred to in general by reference numeral 172. The cradle 172 includes a shank 174 corresponding to the shank 172, but the cradle 172 is adapted to be utilized in conjunction with a support arm 176 corresponding to the support arm 102 but whose lower downwardly offset rear end 178 corresponding to the rear end 106 has a small diameter bore 180 formed therethrough which snugly receives the lower end of the shank 174 therethrough. The shank 174 is adjustably supported from the lower end portion 178 by means of an upper jamb nut 182 threaded on the shank 174 above the lower end portion 178 and a lower thumb nut 184 threaded on that portion of the shank 174 projecting below the lower end portion 178.

With attention now invited more specifically to FIG. 13 of the drawings, there will be seen a third form of cane-crutch assembly referred to in general by the reference numeral 186. The cane-crutch assembly 186 is similar to the cane-crutch assembly 10, except that the assembly 186 does not include sleeve blocks corresponding to the sleeve blocks 52 and 54 and the cradle 188 thereof is supported in fixed position between the portions 190 corresponding to the portions 48 and 50 by means of a pair of fasteners 192.

With attention again invited more specifically to FIGS. 1, 2 and 3 of the drawings, it will be seen tht an elongated edge upstanding and adjustable length wide strap assembly 194 is provided and includes opposite end hem portions 196 which are loosely telescopingly engaged downwardly over one of the sections 100 and the shank 70 of the cane 68. The strap assembly 194 is utilized to embrace the forward portion of the leg disposed immediately above the knee engaged in the forward end of the cradle 78. Also, it will be seen from FIG. 13 of the drawings that the assembly 186 includes a cane 196 corresponding to the cane 86 and a strap assembly 198 corresponding to the strap assembly 194.

It will, of course, be understood that the interior of the cradle 78 as well as the interior of the cradle 188 and the similar component of the assembly 130 illustrated in FIG. 10 will be provided with thick padding (not shown). Further, the assembly 130 illustrated in FIG. 10 does not include a rear cradle such as the cradle 120 or the cradle 122 although such a rear cradle could be provided. Further, a rear cradle could also be provided on the simplified form of assembly 186 illustrated in FIG. 13.

It is also pointed out that the member 12 includes vertically spaced diametric bores formed therethrough whereby the fasteners 42 may be used to secure the member 12 in various extended positions relative to the lower ends of the lower end portions 38 and 40. Further, one fastener 42 may be removed and the other fastener 42 used as a pivot fastener whereby the member 12 may be swung to a folded position similar to that of the member 138 in FIG. 10.

The upper end of the member 12 includes a small diameter upwardly opening recess in which a plurality of the Allen wrenches W and W' may be removably stored. The wrench W is of a size to be used on the fasteners 42 and 104 and in the blind bores 22 and 32 of FIG. 7 while the wrench W' is to be used on the fasteners 76.

The foregoing is considered as illustrative only of the principles of the invention. Further, since numerous modifications and changes will readily occur to those slilled in the art, it is not desired to limit the invention to the exact construction and operation shown and described, and accordingly all suitable modifications and equivalents may be resorted to, falling within the scope of the invention.

What is claimed as new is as follows:

1. A crutch cane including an upright having upper and lower ends, the lower end of said upright including end means for frictionally engaging an upwardly facing support surface, an upwardly opening knee and lower leg receiving cradle support from said upright spaced above said lower end, the upper end of said upright including a horizontal hand grip, said cradle defining an elongated generally horizontal upwardly opening trough, one end of said cradle including an outwardly convex end wall closing the corresponding end of said trough, wherein said upright including horizontal spaced apart upright portions between which said cradle is disposed, and an adjustable length, elongated, horizontal and longitudinal edge upstanding wide strap assembly extending loosely between said spaced apart upright portions spaced above one end of said cradle and longitudinally bowed with its convex side facing outwardly of said one end of said cradle.

2. A crutch cane including an upright having upper and lower ends, the lower end of said upright including end means for frictionally engaging an upwardly facing support surface, an upwardly opening knee and lower leg receiving cradle supported from said upright spaced above said lower end, the upper end of said upright including a horizontal hand grip, said upright and hand grip including coacting mounting means supporting said hand grip from said upright for angular displacement relative thereto about an axis generally paralleling said upright.

3. The combination of claim 2 wherein said coacting mounting means also includes means supporting said hand grip from said upright for vertical shifting relative thereto.

4. The combination of claim 3 wherein the last mentioned means includes means operative to progressively yieldingly resist downward shifting of said hand grip relative to said upright toward a lower limit position of said hand grip.

5. The combination of claim 3 wherein the last mentioned means includes means operative to progressively yieldingly resist upward shifting of said hand grip relative to said upright.

6. The combination of claim 3 wherein the last mentioned means includes means operative to progressively yieldingly resist upward shifting of said hand grip relative to said upright, and means operative downward shifting of said hand grip relative to said upright toward a lower limit position of said hand grip.

7. The combination of claim 2 wherein said end means includes a vertically adjustable foot member.

8. The combination of claim 7 wherein said foot member is threadedly supported for said upright.

9. The combination of claim 8 wherein said foot member includes a non-slip cup shaped tip removably telescoped upwardly over the lower end thereof.

10. The combination of claim 8 wherein said foot member includes an upstanding threaded support shank threadedly engaged with said upright, the lower end of said support shank including a diametrically enlarged load bearing pad assembly universally supported therefrom.

11. The combination of claim 10 wherein said pad assembly includes a large plan area downwardly facing abutment surface and a non-slip panel removably supported thereunder.

12. A crutch cane including an upright having upper and lower ends, the lower end of said upright including end means for frictionally gripping an upwardly facing support surface, an upwardly opening knee and lower leg receiving cradle supported from said upright spaced above said lower end, the upper end of said upright including a horizontal hand grip, said cradle and upright including coacting support means mounting said cradle on said upright for selective angular displacement relative thereto about a horizontal axis, said cradle defining an elongated trough extending transversely of the last mentioned axis.

13. The combination of claim 12 wherein said upright and hand grip include coacting mounting means supporting said hand grip and said upright for angular displacement relative thereto about an axis generally paralleling said upright.

14. The combination of claim 12 wherein one end of said cradle includes an outwardly convex end wall closing the corresponding end of said trough.

15. The combination of claim 14 wherein said upright includes horizontally spaced apart upright portions between which said cradle is disposed, and an adjustable length, elongated, horizontal and longitudinal edge upstanding wide strap assembly extending loosely between said spaced apart upright portions spaced above one end of said cradle and longitudinally bowed with its convex side facing outwardly of said one end of said cradle.

16. The combination of claim 15 wherein said cradle end wall closing said one cradle end conforms, generally, to the radius of curvature of said strap assembly and is vertically registered beneath the latter.

17. The combination of claim 16 wherein said upright and hand grip include coacting mounting means supporting said hand grip from said upright for angular displacement relative thereto about an axis generally paralleling said upright.

18. The combination of claim 17 wherein said coacting mounting means also includes means supporting said hand grip from said upright for vertical shifting relative thereto.

19. A crutch-cane including an upright having upper and lower ends, the lower end of said upright including end means for frictionally gripping an upwardly facing support surface, an upwardly opening knee and lower leg receiving cradle supported from said upright spaced above said lower end, the upper end of said upright including a hand grip, said cradle and upright including coacting support means mounting said cradle on said upright for selective angular displacement relative thereto about a horizontal axis, said cradle defining an elongated trough extending transversely of the last mentioned axis.

20. The combination of claim 19 wherein said coacting support means also includes means operative to releasably secure said cradle in selected angularly displaced position relative to said horizontal axis.

21. The combination of claim 19 wherein said upright and hand grip include coacting mounting means supporting said hand grip from said upright for angular displacement relative thereto about an axis generally paralleling said upright, said coacting mounting means also including means operative to releasably retain said hand grip in adjusted angular position relative to said upright.

22. The combination of claim 19 wherein one end of said cradle including an outwardly convex end wall closing the corresponding end of said trough, the other end of said cradle being open and including an endwise outwardly projecting support arm, the outer end of said arm including a second upwardly opening cradle.

23. The combination of claim 22 wherein said second cradle and arm include coacting means supporting said second cradle from said arm for vertical adjustment relative thereto.

24. The combination of claim 23 wherein the last mentioned coacting means includes means establishing upper and lower limits of shifting of said second cradle relative to said arm and means yieldingly biasing said second cradle toward said upper limit.

25. The combination of claim 24 wherein said upright and hand grip include coacting mounting means supporting said hand grip from said upright for angular displacement relative thereto about an axis generally paralleling said upright.

26. The combination of claim 24 wherein said upright includes horizontally spaced apart upright portions between which said cradle is disposed, and an adjustable length, elongated, horizontal and longitudinal edge upstanding wide strap assembly extending loosely between said spaced apart upright portions spaced above one end of said cradle and longitudinally bowed with its convex side facing outwardly of said one end of said cradle.

27. The combination of claim 26 wherein one end of said cradle including an outwardly convex end wall closing said one cradle end and conforming, generally, to the radius of curvature of said strap assembly and vertically registered beneath the latter.

28. The combination of claim 26 wherein said upright and hand grip include coacting mounting means supporting said hand grip from said upright for angular displacement relative thereto about an axis generally paralleling said upright, said coacting mounting means also including means supporting said hand grip from said upright for vertical shifting relative thereto.

29. The combination of claim 28 wherein the last mentioned means includes means operative to progressively yieldingly resist downward shifting of said hand grip relative to said upright toward a lower limit position of said hand grip.

* * * * *